US012508440B2

(12) United States Patent
Park et al.

(10) Patent No.: US 12,508,440 B2
(45) Date of Patent: Dec. 30, 2025

(54) VIBRATION STIMULATION DEVICE

(71) Applicant: ELECTRONICS AND TELECOMMUNICATIONS RESEARCH INSTITUTE, Daejeon (KR)

(72) Inventors: Kang-Ho Park, Daejeon (KR); Jong Tae Lim, Daejeon (KR); Seung Youl Kang, Daejeon (KR); Sujung Kim, Daejeon (KR); Bock Soon Na, Daejeon (KR); Chan Woo Park, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 859 days.

(21) Appl. No.: 17/833,666

(22) Filed: Jun. 6, 2022

(65) Prior Publication Data

US 2023/0039362 A1 Feb. 9, 2023

(30) Foreign Application Priority Data

Aug. 4, 2021 (KR) ........................ 10-2021-0102590
Oct. 25, 2021 (KR) ........................ 10-2021-0142604

(51) Int. Cl.
*A61H 23/00* (2006.01)
*A61N 5/06* (2006.01)

(52) U.S. Cl.
CPC ......... *A61N 5/0617* (2013.01); *A61H 23/004* (2013.01); *A61N 2005/0633* (2013.01); *A61N 2005/0643* (2013.01); *A61N 2005/065* (2013.01)

(58) Field of Classification Search
CPC .......... A61H 23/004; A61H 2201/0153; A61H 2201/105; A61H 23/00; A61H 2023/002; A61H 23/006; A61H 23/02; A61H 2023/0209; A61H 2023/0227; A61H 23/0236; A61H 23/0245; A61H 23/0254; A61H 2023/0272–029; A61H 23/04; A61H 1/005; A61N 2005/0633; A61N 5/0617; A61N 2005/0644; A61N 2005/0652; A61N 2005/0659; A61M 35/003; A61M 2210/06
See application file for complete search history.

(56) References Cited

U.S. PATENT DOCUMENTS 7,207,953 B1 * 4/2007 Goicaj .................. A61H 23/02 601/134
7,722,655 B2 5/2010 Lee
9,023,283 B2 5/2015 Yamaguchi
(Continued)

FOREIGN PATENT DOCUMENTS

KR 10-2010-0007873 A 2/2001
KR 100546080 B1 1/2006
(Continued)

*Primary Examiner* — Margaret M Luarca
*Assistant Examiner* — Sarah B Lederer

(57) ABSTRACT

Disclosed is a vibration stimulation device. The vibration stimulation device includes a box having a cavity, vibrators disposed in the cavity; light emitting elements disposed between the vibrators or disposed on the vibrators, an upper vibration layer configured to connect the vibrators and the light emitting elements to edges of the box on the cavity, and bumps disposed on the vibrators.

17 Claims, 18 Drawing Sheets

(56) References Cited

U.S. PATENT DOCUMENTS

| | | | | |
|---|---|---|---|---|
| 9,744,096 | B2 | 8/2017 | Park et al. | |
| 2007/0167885 | A1* | 7/2007 | Moon | A61H 23/0263 601/67 |
| 2008/0275532 | A1* | 11/2008 | Yamazaki | A46B 13/023 607/88 |
| 2009/0234253 | A1* | 9/2009 | Vandenbelt | A46B 13/023 15/105 |
| 2011/0092863 | A1 | 4/2011 | Kim et al. | |
| 2011/0293479 | A1 | 12/2011 | Hong et al. | |
| 2013/0261515 | A1 | 10/2013 | Choi et al. | |
| 2018/0140860 | A1* | 5/2018 | Ledany | A61N 5/06 |
| 2020/0179667 | A1* | 6/2020 | Wang | A61N 5/062 |
| 2020/0230021 | A1* | 7/2020 | Pisharodi | A61H 23/0263 |
| 2020/0293111 | A1 | 9/2020 | Gwak | |
| 2021/0213216 | A1* | 7/2021 | Smith | A61H 31/00 |

FOREIGN PATENT DOCUMENTS

| | | | |
|---|---|---|---|
| KR | 10-0682407 | B1 | 2/2007 |
| KR | 10-0851621 | B1 | 8/2008 |
| KR | 10-0903152 | B1 | 6/2009 |
| KR | 100926901 | B1 * | 11/2009 |
| KR | 100995427 | B1 | 11/2010 |
| KR | 10-2013-0031172 | A | 3/2013 |
| KR | 10-2014-0052667 | A | 5/2014 |
| KR | 101450762 | B1 | 10/2014 |
| KR | 102200556 | B1 | 1/2021 |
| KR | 10-2021-0052152 | A | 5/2021 |

* cited by examiner

VIBRATION STIMULATION DEVICE

CROSS-REFERENCE TO RELATED APPLICATIONS

This U.S. non-provisional patent application claims priority under 35 U.S.C. § 119 of Korean Patent Application Nos. 10-2021-0102590, filed on Aug. 4, 2021, and 10-2021-0142604, filed on Oct. 25, 2021, the entire contents of which are hereby incorporated by reference.

BACKGROUND

The present disclosure herein relates to a vibration stimulation device, and more particularly, to a vibration stimulation device capable of irradiating light.

In general, a vibrating element may be an actuator element generating and transferring a vibration by using an electric motor, a piezoelectric element, and a capacitive element. The vibrating elements may be arranged in an array form and individually controlled. The vibrating element may be realized into a vibration mask, a vibration helmet, a vibration band, and a vibration glove. The vibrating element may provide various types of vibration stimulations to subcutaneous organs and tissues of various human body portions to increase a stimulation effect and improve user's convenience for skin care and hair and scalp care.

SUMMARY

The present disclosure provides a vibration stimulation device capable of heating and/or treating a human body by using light.

An embodiment of the inventive concept provides a vibration stimulation device including: a box having a cavity; vibrators disposed in the cavity; light emitting elements disposed between the vibrators or disposed on the vibrators; an upper vibration layer configured to connect the vibrators and the light emitting elements to edges of the box on the cavity; and bumps disposed on the vibrators.

In an embodiment, the vibration stimulation device may further include pockets that respectively surround the vibrators.

In an embodiment, when the vibrators are disposed on the upper vibration layer, each of the pockets may surround top and side surfaces of each of the vibrators.

In an embodiment, the vibration stimulation device may further include a protection layer disposed on each of the light emitting elements.

In an embodiment, the vibration stimulation device may further include a lower vibration layer disposed below the vibrators.

In an embodiment, each of the bumps may have a shape of multiple tips.

In an embodiment, the vibration stimulation device may further include weights disposed on or below the vibrators.

In an embodiment, the vibration stimulation device may further include weight pockets that respectively surround the weights.

In an embodiment, the vibration stimulation device may further include stands disposed between the vibrators and an inner bottom surface of the box.

In an embodiment, the vibration stimulation device may further include an elastic body disposed between the stands and an inner bottom surface of the box.

In an embodiment, the elastic body may include a rubber block or a spring.

In an embodiment, the box may have trenches disposed below the vibrators.

In an embodiment, the vibration stimulation device may further include bands connected to both sides of the box.

In an embodiment, the vibration stimulation device may further include: a case that surrounds a lower portion of the box; and a support disposed between the box and an inner bottom surface of the case.

In an embodiment, the support may include a rubber block or a spring.

In an embodiment, the box may be provided in plurality in the case, and the vibration stimulation device may further include hinges between the plurality of boxes.

In an embodiment, the vibration stimulation device may further include thermoelectric elements that are respectively disposed on the vibrators and respectively disposed in the bumps.

In an embodiment, each of the thermoelectric elements may include: a lower substrate; lower electrodes disposed on the lower substrate; first and second type semiconductors disposed on the lower electrodes; upper electrodes disposed on the first and second type semiconductors; and an upper substrate disposed on the upper electrodes.

In an embodiment, the box may have trenches or recesses that are respectively disposed below the vibrators.

BRIEF DESCRIPTION OF THE FIGURES

The accompanying drawings are included to provide a further understanding of the inventive concept, and are incorporated in and constitute a part of this specification. The drawings illustrate embodiments of the inventive concept and, together with the description, serve to explain principles of the inventive concept. In the drawings.

DETAILED DESCRIPTION

Figure 1:
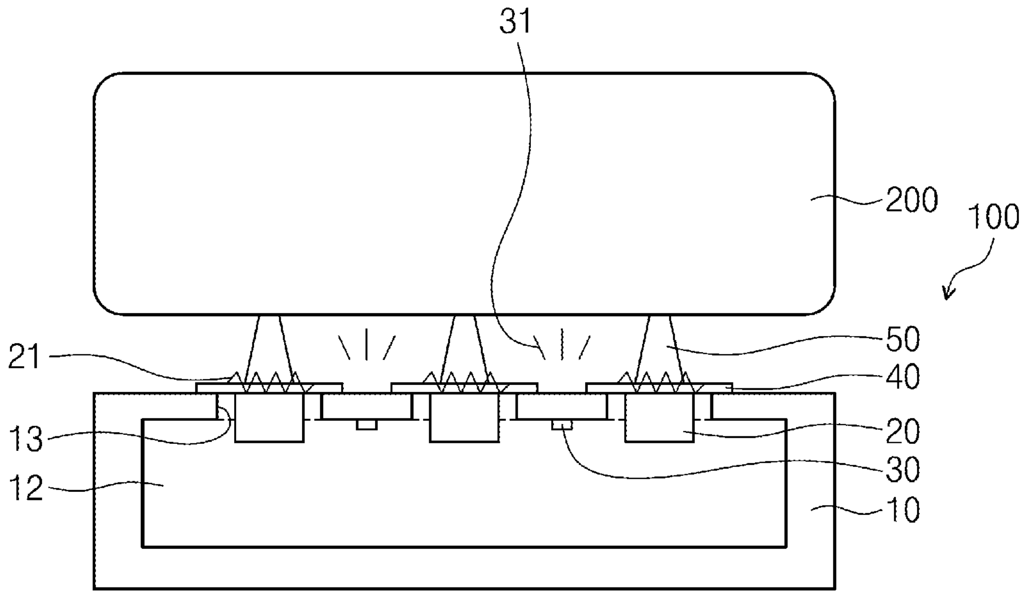
FIG. 1 is a cross-sectional view illustrating an example of a vibration stimulation device according to an embodiment of the inventive concept.

Hereinafter, preferred embodiments of the inventive concept will be described in detail with reference to the accompanying drawings. Advantages and features of the present invention, and implementation methods thereof will be clarified through following embodiments described with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Like reference numerals refer to like elements throughout.

In the following description, the technical terms are used only for explaining a specific embodiment while not limiting the present invention. In the specification, the terms of a singular form may include plural forms unless referred to the contrary. The meaning of “include,” “comprise,” “including,” or “comprising,” specifies a property, a region, a fixed number, a step, a process, an element and/or a component but does not exclude other properties, regions, fixed numbers, steps, processes, elements and/or components. Since preferred embodiments are provided below, the order of the reference numerals given in the description is not limited thereto.

Additionally, the embodiment in the detailed description will be described with sectional views as ideal exemplary views of the present invention. In the drawings, a substrate, an electrode, and an elastic thin film of mirrors may be exaggerated for effective descriptions of technical features. Accordingly, shapes of the exemplary views may be modified according to manufacturing techniques and/or allowable errors. Therefore, the embodiments of the present invention are not limited to the specific shape illustrated in the exemplary views, but may include other shapes that may be created according to manufacturing processes.

Figure 2:
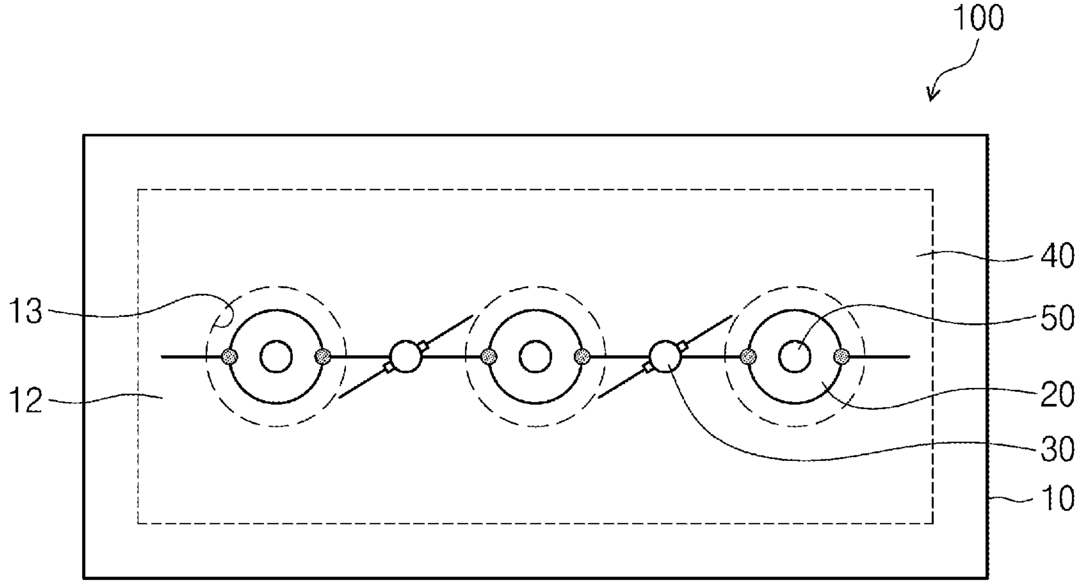
FIG. 2 is a plan view illustrating an example of the vibration stimulation device in FIG. 1.

FIG. 1 is a view illustrating an example of a vibration stimulation device 100 according to an embodiment of the inventive concept. FIG. 2 is a view illustrating an example of the vibration stimulation device 100 in FIG. 1.

Referring to FIGS. 1 and 2, the vibration stimulation device 100 according to an embodiment of the inventive concept may include a box 10, vibrators 20, light emitting elements 30, an upper vibration layer 40, and bumps 50.

The box 10 may have a cavity 12. The cavity 12 may be disposed at a center of the box 10. Each of the box 10 and the cavity 12 may have a rectangular shape in term of a plane. The box 10 may be transparent. Alternatively, the box 10 may be opaque. However, the embodiment of the inventive concept is not limited thereto. For example, the box 10 may include plastic, wood, metal, or ceramic.

The vibrators 20 may be disposed in or on the cavity 12. The vibrators 20 may be disposed in an inlet 13 of the cavity 12. The vibrators 20 may generate a vibration to stimulate a human body 200. For example, the vibrators 20 may include a piezoelectric element, an electric motor, or a capacitive element. However, the embodiment of the inventive concept is not limited thereto.

The light emitting elements 30 may be disposed between the vibrators 20. The light emitting elements 30 may be disposed in the cavity 12. Alternatively, the light emitting elements 30 may be disposed on the box 10. The light emitting elements 30 may generate light to heat and/or treat the human body 200. For example, the light emitting elements 30 may include a LED and a LD. However, the embodiment of the inventive concept is not limited thereto.

The upper vibration layer 40 may be disposed on the box 10. The upper vibration layer 40 may support the vibrators 20 and the light emitting elements 30 on the cavity 20. The upper vibration layer 40 may connect the vibrators 20 and the light emitting elements 30 to edges of the box 10 at an outer portion of the cavity 12. The upper vibration layer 40 may include a vinyl film such as PDMS, PMMA, Ecoflex, elastomer, silicone, urethane, and polyacryl or a rubber film. However, the embodiment of the inventive concept is not limited thereto.

The bumps 50 may be disposed on the vibrators 20. The bumps 50 may contact the human body 200. The bumps 50 may transfer vibration energy of the vibrators 20 to the human body 200. Each of the bumps 50 may include an elastic material such as PDMS, PMMA, Ecoflex, elastomer, silicone, urethane, polyacryl, rubber, cellulose, gel, sponge, or foam. The bumps 50 may include plastic, metal, ceramic, or a wood. However, the embodiment of the inventive concept is not limited thereto.

Thus, the vibration stimulation device 100 according to an embodiment of the inventive concept may stimulate and treat the human body 200 by using the vibrators 20 and the light emitting elements 300.

Figure 3:
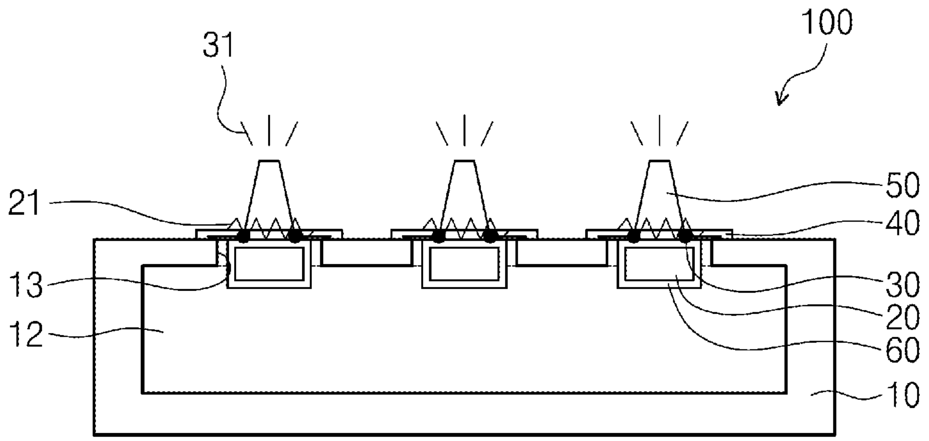
FIG. 3 is a cross-sectional view illustrating an example of the vibration stimulation device according to an embodiment of the inventive concept.

FIG. 3 is a view illustrating an example of the vibration stimulation device 100 according to an embodiment of the inventive concept.

Referring to FIG. 3, the vibration stimulation device 100 may further include pockets 60. Each of the pockets 60 may surround a portion of each of the vibrators 20. Each of the pockets 60 may surround a lower portion and a side portion of each of the vibrators 20. The pockets 60 may protect the vibrators 20. Each of the pockets 60 may include a rubber film such as PDMS, PMMA, Ecoflex, elastomer, silicone, urethane, and polyacryl. However, the embodiment of the inventive concept is not limited thereto.

The light emitting elements 30 may be disposed between the vibrators 20 and the bumps 50. The bumps 50 may be transparent. The bumps 50 may emit light of the light emitting elements 30 to the outside.

The box 10 may be configured as same as that in FIG. 1.

Figure 4:
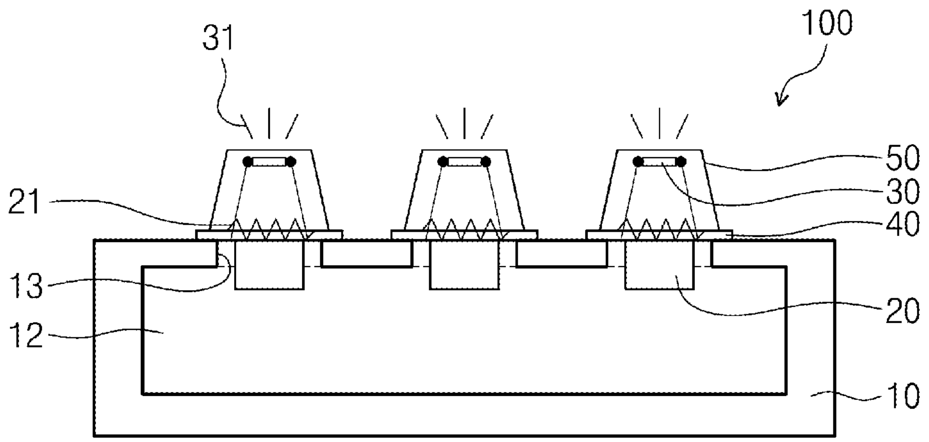
FIG. 4 is a cross-sectional view illustrating an example of the vibration stimulation device according to an embodiment of the inventive concept.

FIG. 4 is a view illustrating an example of the vibration stimulation device 100 according to an embodiment of the inventive concept.

Referring to FIG. 4, the light emitting elements 30 may be disposed on the bumps 50. For example, the light emitting elements 30 may be disposed in or on tips of the bumps 50.

Although not shown, the light emitting elements 30 may contact the human body 200. The light emitting elements 30 may heat or treat the human body 200.

The box 10, the vibrators 20, the upper vibration layer 40, and the bumps 50 may be configured as same as those in FIG. 1.

Figure 5:
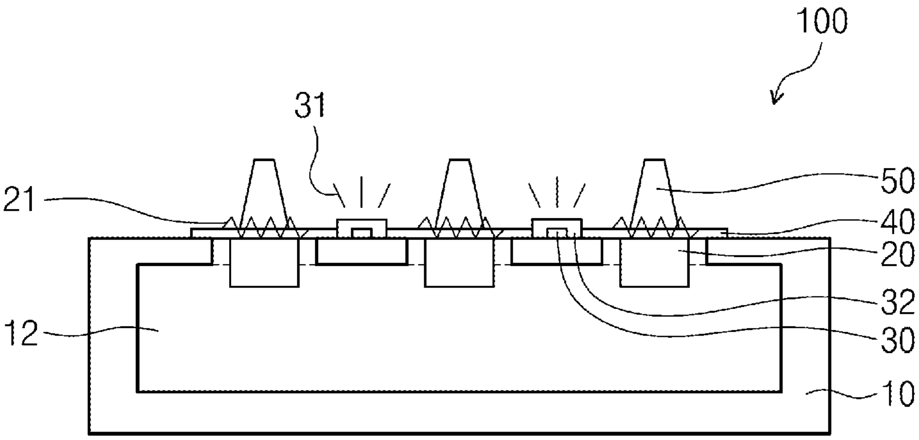
FIG. 5 is a cross-sectional view illustrating an example of the vibration stimulation device according to an embodiment of the inventive concept.

FIG. 5 is a view illustrating an example of the vibration stimulation device 100 according to an embodiment of the inventive concept.

Referring to FIG. 5, a protection layer 32 may be disposed on each of the light emitting elements 30. The protection layer 32 may protect the light emitting elements 30 from external pollution or impact and a vibration 21 of the vibrators 20. The protection layer 32 may include glass. However, the embodiment of the inventive concept is not limited thereto.

Figure 6:
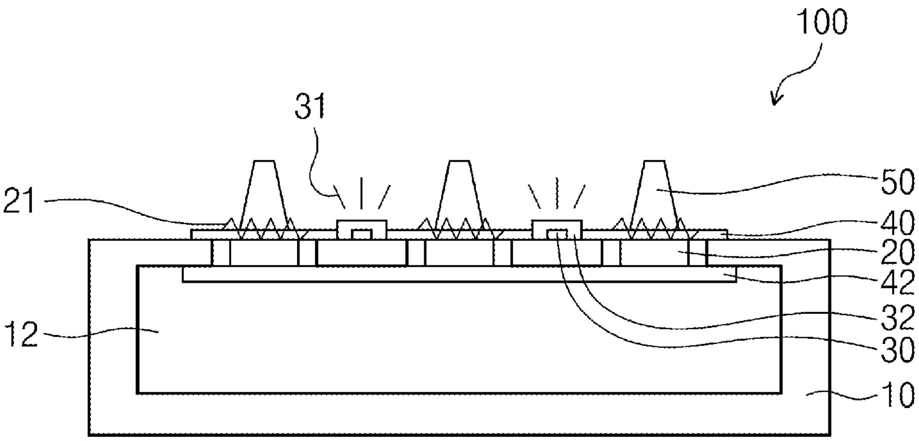
FIG. 6 is a cross-sectional view illustrating an example of the vibration stimulation device according to an embodiment of the inventive concept.

FIG. 6 is a view illustrating an example of the vibration stimulation device 100 according to an embodiment of the inventive concept.

Referring to FIG. 6, the vibration stimulation device 100 according to an embodiment of the inventive concept may further include a lower vibration layer 42. The lower vibration layer 42 may be disposed in the cavity 12. The lower vibration layer 42 may be disposed below the vibrators 20. The lower vibration layer 42 may support the vibrators 20. The lower vibration layer 42 may include a vinyl film such as PDMS, PMMA, Ecoflex, elastomer, silicone, urethane, and polyacryl or a rubber film.

The light emitting elements 30 may be disposed on the box 10. The light emitting elements 30 may be disposed between the vibrators 20.

The box 10, the vibrators 20, the upper vibration layer 40, and the bumps 50 may be configured as same as those in FIG. 1.

Figure 7:
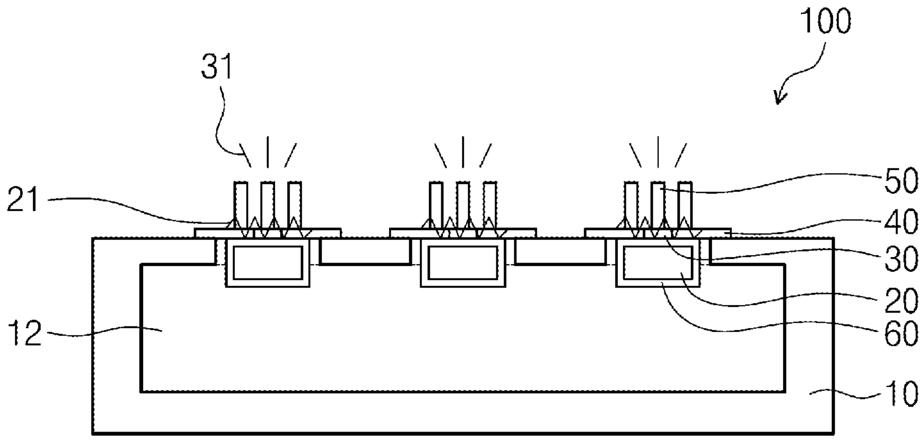
FIG. 7 is a cross-sectional view illustrating an example of the vibration stimulation device according to an embodiment of the inventive concept.

FIG. 7 is a view illustrating an example of the vibration stimulation device 100 according to an embodiment of the inventive concept.

Referring to FIG. 7, each of the bumps 50 may have a shape of multiple tips. Alternatively, each of the bumps 50 may have a comb shape. However, the embodiment of the inventive concept is not limited thereto. For example, each of the bumps 50 may include PDMS, PMMA, Ecoflex, elastomer, silicone, urethane, polyacryl, or plastic.

The light emitting elements 30 may be disposed between the vibrators 20 and the bumps 50. Each of the pockets 60 may surround a lower portion and a side surface of each of the vibrators 20.

The box 10, the vibrators 20, the upper vibration layer 40, and the bumps 50 may be configured as same as those in FIG. 1.

Figure 8:
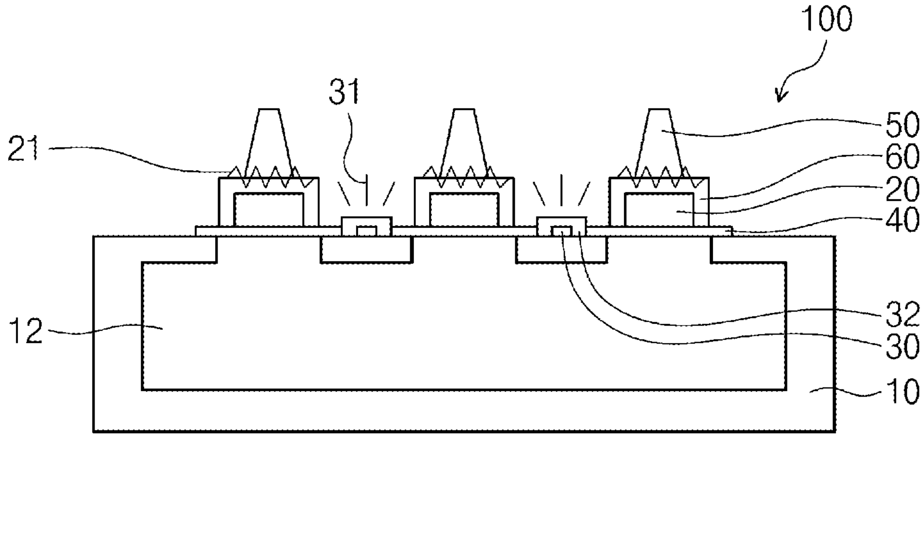
FIG. 8 is a cross-sectional view illustrating an example of the vibration stimulation device according to an embodiment of the inventive concept.

FIG. 8 is a view illustrating an example of the vibration stimulation device 100 according to an embodiment of the inventive concept.

Referring to FIG. 8, the vibrators 20 and the pockets 60 may be disposed on the upper vibration layer 40. The light emitting elements 60 may be disposed between the vibrators 20 and the bumps 50.

The light emitting elements 30 and the protection layer 32 may be disposed between the pockets 60. The box 10 may be configured as same as that in FIG. 1.

Figure 9:
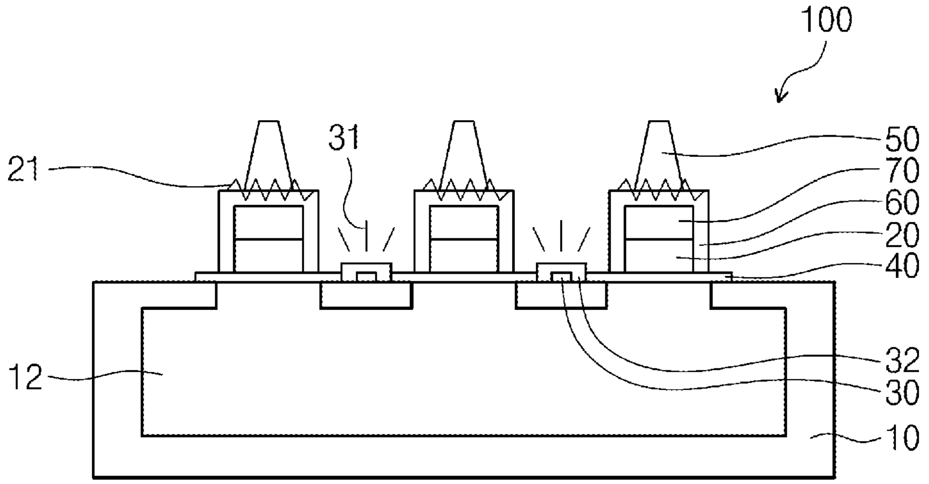
FIG. 9 is a cross-sectional view illustrating an example of the vibration stimulation device according to an embodiment of the inventive concept.

FIG. 9 is a view illustrating an example of the vibration stimulation device 100 according to an embodiment of the inventive concept.

Referring to FIG. 9, the vibration stimulation device 100 according to an embodiment of the inventive concept may further include weights 70. The weights 70 may be disposed on the vibrators 20. The weights 70 may increase a vibrating mass to adjust an output and a frequency of the vibration 21 of each of the vibrators 20.

Each of the pockets 60 may surround a side surface and an upper portion of each of the vibrators 20 and the weights 70. The bumps 50 may be disposed on the pockets 60. The upper vibration layer 40 may support the vibrators 20, the weights 70, and the pockets 60. The light emitting elements 30 and the protection layer 32 may be disposed between the pockets 60.

The box 10 may be configured as same as that in FIG. 1.

Figure 10:
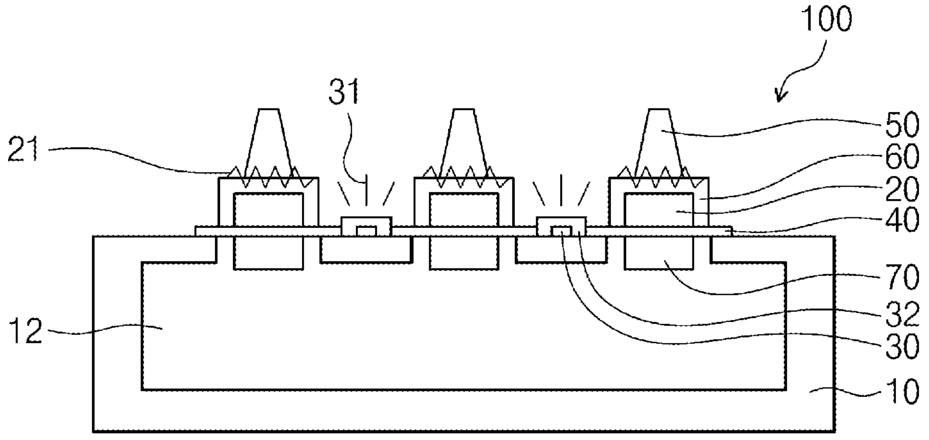
FIG. 10 is a cross-sectional view illustrating an example of the vibration stimulation device according to an embodiment of the inventive concept.

FIG. 10 is a view illustrating an example of the vibration stimulation device 100 according to an embodiment of the inventive concept.

Referring to FIG. 10, the weights 70 may be disposed below the vibrators 20. The weights 70 may be disposed in the cavity 12.

The box 10, the light emitting elements 30, the protection layer 32, the upper vibration layer 40, the bumps 50, and the pockets 60 may be configured as same as those in FIG. 9.

Figure 11:
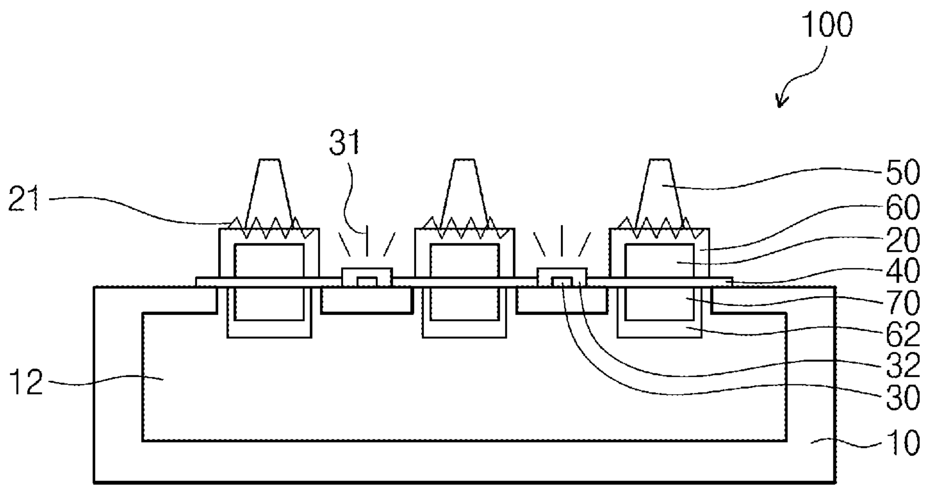
FIG. 11 is a cross-sectional view illustrating an example of the vibration stimulation device according to an embodiment of the inventive concept.

FIG. 11 is a view illustrating an example of the vibration stimulation device 100 according to an embodiment of the inventive concept.

Referring to FIG. 11, the vibration stimulation device 100 according to an embodiment of the inventive concept may further include weight pockets 62. Each of the weight pockets 62 may surround a lower portion and a side surface of each of the weights 70. The weight pockets 62 may protect the weights 70.

The box 10, the vibrators 20, the light emitting elements 30, the protection layer 32, the upper vibration layer 40, the bumps 50, and the pockets 60 may be configured as same as those in FIG. 10.

Figure 12:
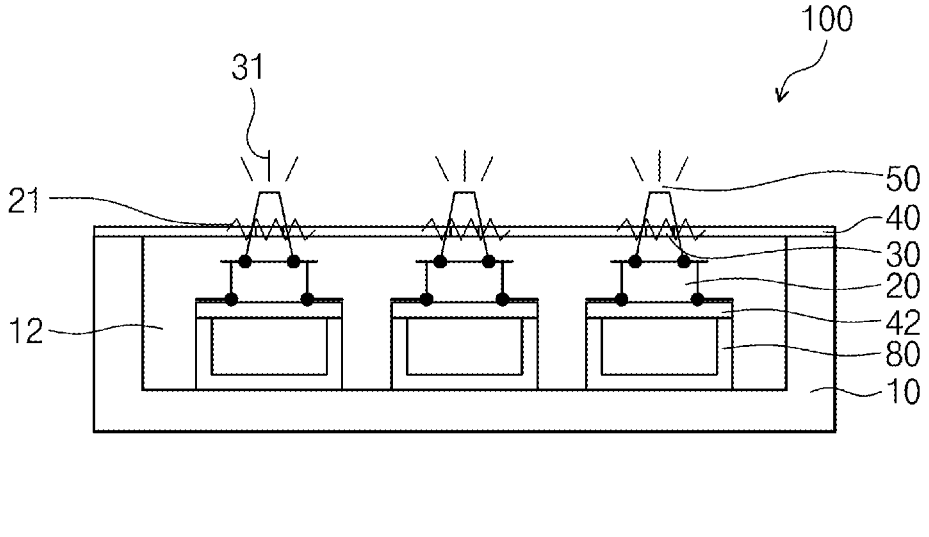
FIG. 12 is a cross-sectional view illustrating an example of the vibration stimulation device according to an embodiment of the inventive concept.

FIG. 12 is a view illustrating an example of the vibration stimulation device 100 according to an embodiment of the inventive concept.

Referring to FIG. 12, the vibration stimulation device 100 according to an embodiment of the inventive concept may further include stands 80. The stands 80 may be disposed between an inner bottom surface of the box 10 and the lower vibration layer 42. The stands 80 and the lower vibration layer 42 may support the vibrators 20 and the light emitting elements 30 from the inner bottom surface of the box 10. Each of the stands 80 may include plastic, metal, ceramic, or wood. However, the embodiment of the inventive concept is not limited thereto.

The light emitting elements 30 may be disposed in bumps 50, respectively. The upper vibration layer 40 may connect the bumps 50 and the light emitting elements 30 to edges of the box 10.

Figure 13:
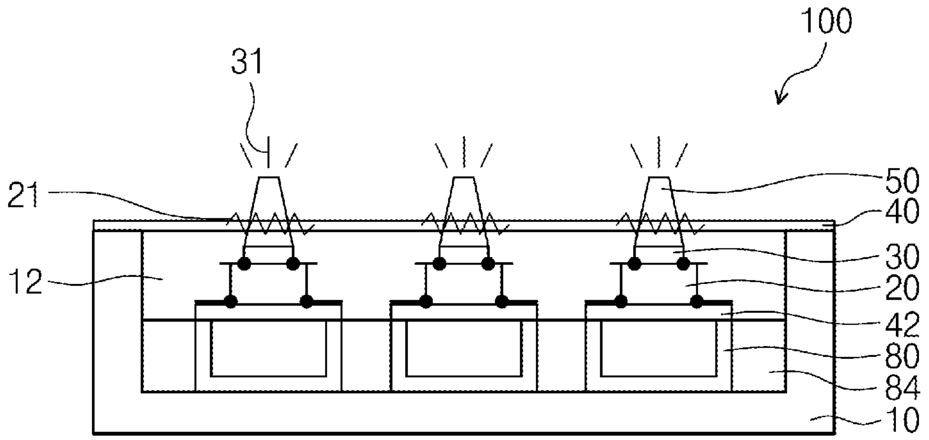
FIG. 13 is a cross-sectional view illustrating an example of the vibration stimulation device according to an embodiment of the inventive concept.

FIG. 13 is a view illustrating an example of the vibration stimulation device 100 according to an embodiment of the inventive concept.

Referring to FIG. 13, the vibration stimulation device 100 according to an embodiment of the inventive concept may further include an elastic body 84. The elastic body 84 may be disposed between the stands 80. The elastic body 84 may be disposed between inner sidewalls of the box 10 and sidewalls of the stands 80. The elastic body 84 may reduce a vibration noise between the stands 80. For example, the elastic body 84 may include a polymer block or a rubber block. However, the embodiment of the inventive concept is not limited thereto.

The lower vibration layer 42, the vibrators 20, the light emitting elements 30, the upper vibration layer 40, and the bumps 50 may be stacked.

Figure 14:
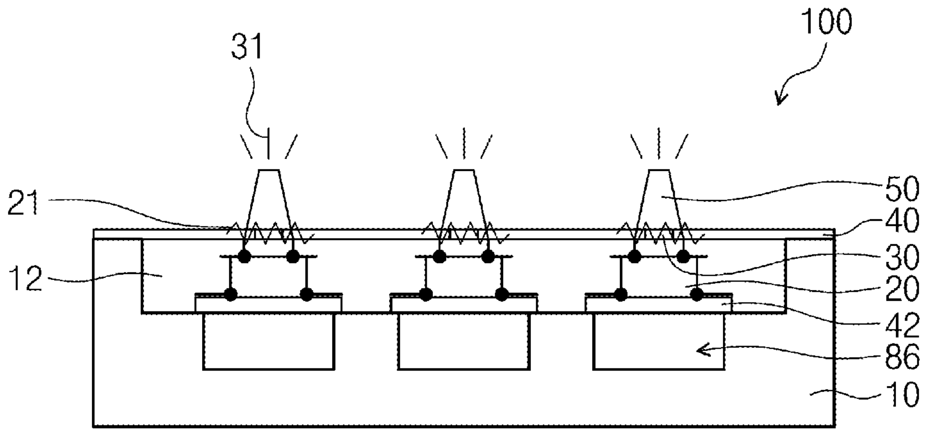
FIG. 14 is a cross-sectional view illustrating an example of the vibration stimulation device according to an embodiment of the inventive concept.

FIG. 14 is a view illustrating an example of the vibration stimulation device 100 according to an embodiment of the inventive concept.

Referring to FIG. 14, the box 10 may have trenches 86 or recesses of an inner bottom thereof. The trenches 86 may be disposed below the lower vibration layer 42. The trenches 86 may decrease collision of the box 10 with the lower vibration layer 42 and the vibrators 20.

The vibrators 20, the light emitting elements 30, the upper vibration layer 40, and the bumps 50 may be configured as same as those in FIG. 13.

Figure 15:
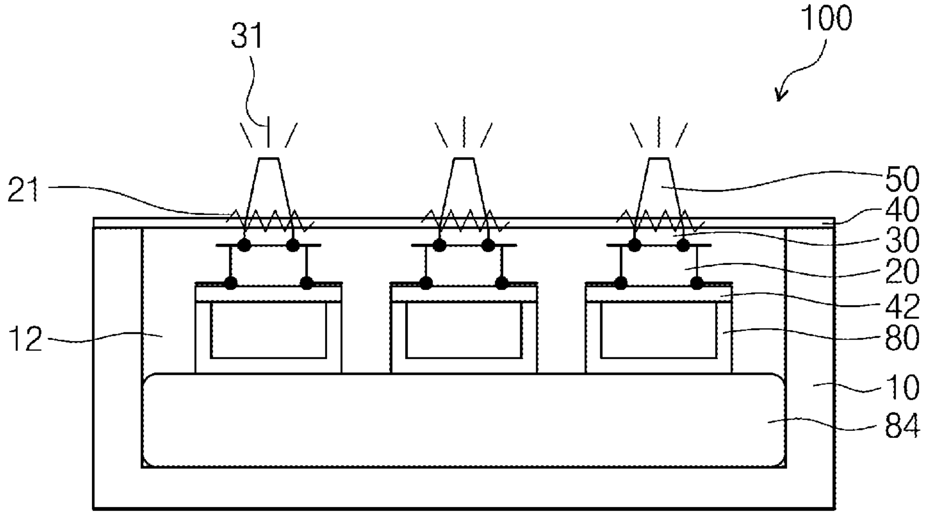
FIG. 15 is a cross-sectional view illustrating an example of the vibration stimulation device according to an embodiment of the inventive concept.

FIG. 15 is a view illustrating an example of the vibration stimulation device 100 according to an embodiment of the inventive concept.

Referring to FIG. 15, the stands 80 may be disposed on the elastic body 84. The elastic body 84 may reduce transmission of the vibration 21 of the stands 80 to the box 10.

The lower vibration layer 42, the vibrators 20, the light emitting elements 30, the upper vibration layer 40, and the bumps 50 may be configured as same as those in FIG. 13.

Figure 16:
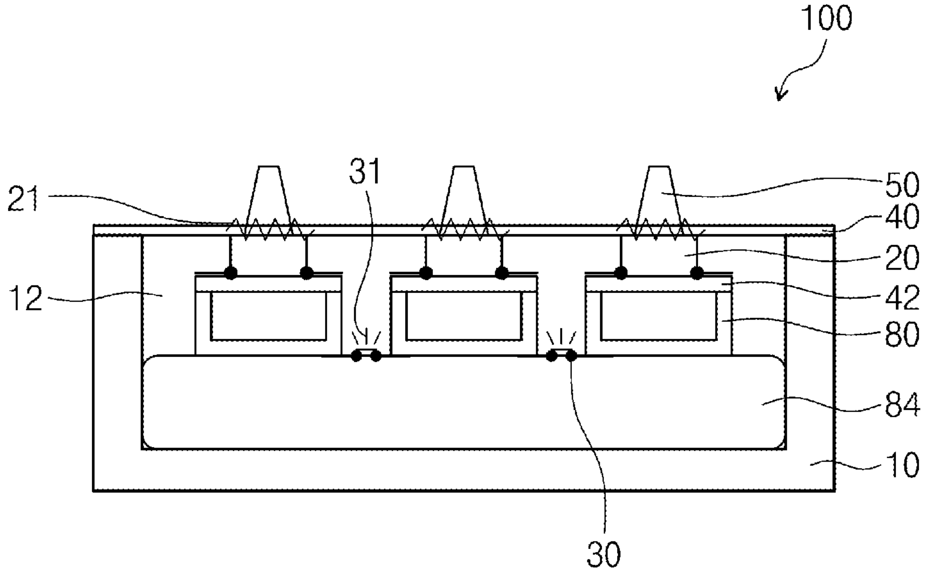
FIG. 16 is a cross-sectional view illustrating an example of the vibration stimulation device according to an embodiment of the inventive concept.

FIG. 16 is a view illustrating an example of the vibration stimulation device 100 according to an embodiment of the inventive concept.

Referring to FIG. 16, the light emitting elements 30 may be disposed between the stands 80. Light 31 of the light emitting elements 30 may be reflected by sidewalls of the stands 80. Each of the stands 80 may include metal. However, the embodiment of the inventive concept is not limited thereto.

The lower vibration layer 42, the vibrators 20, the upper vibration layer 40, and the bumps 50 may be stacked on the stands 80. The box 10 may be configured as same as that in FIG. 13.

Figure 17:
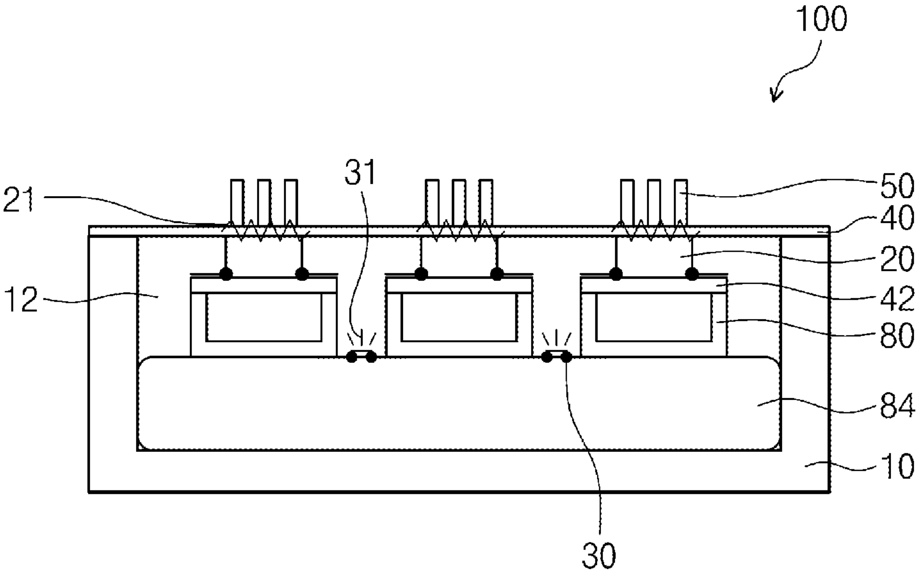
FIG. 17 is a cross-sectional view illustrating an example of the vibration stimulation device according to an embodiment of the inventive concept.

FIG. 17 is a view illustrating an example of the vibration stimulation device 100 according to an embodiment of the inventive concept.

Referring to FIG. 17, each of the bumps 50 may have a shape of multiple tips.

The box 10, the elastic body 84, the stands 80, the lower vibration layer 42, the vibrators 20, the upper vibration layer 40, and the bumps 50 may be configured as same as those in FIG. 16.

Figure 18:
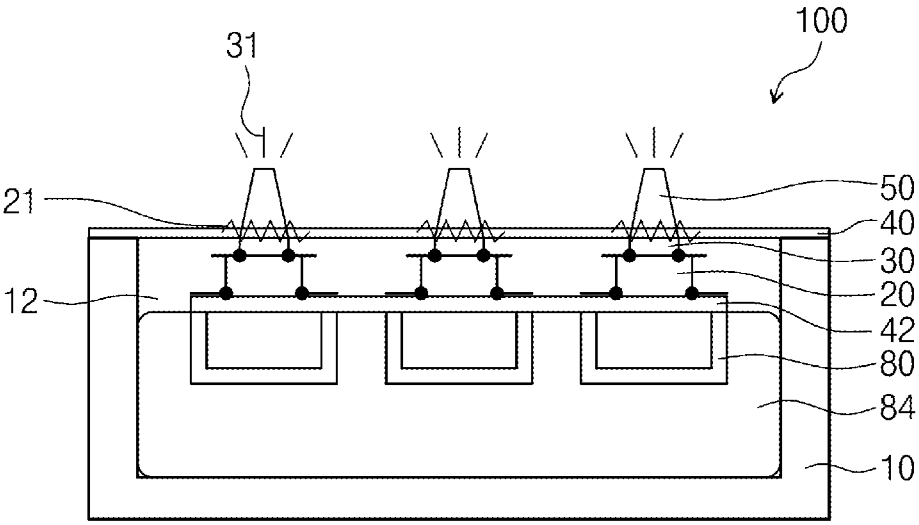
FIG. 18 is a cross-sectional view illustrating an example of the vibration stimulation device according to an embodiment of the inventive concept.

FIG. 18 is a view illustrating an example of the vibration stimulation device 100 according to an embodiment of the inventive concept.

Referring to FIG. 18, the stands 80 may be disposed in the elastic body 84. The elastic body 84 may reduce interference of the vibration 21 between the stands 80.

The box 10, the lower vibration layer 42, the vibrators 20, the light emitting elements 30, the upper vibration layer 40, and the bumps 50 may be configured as same as those in FIG. 15.

Figure 19:
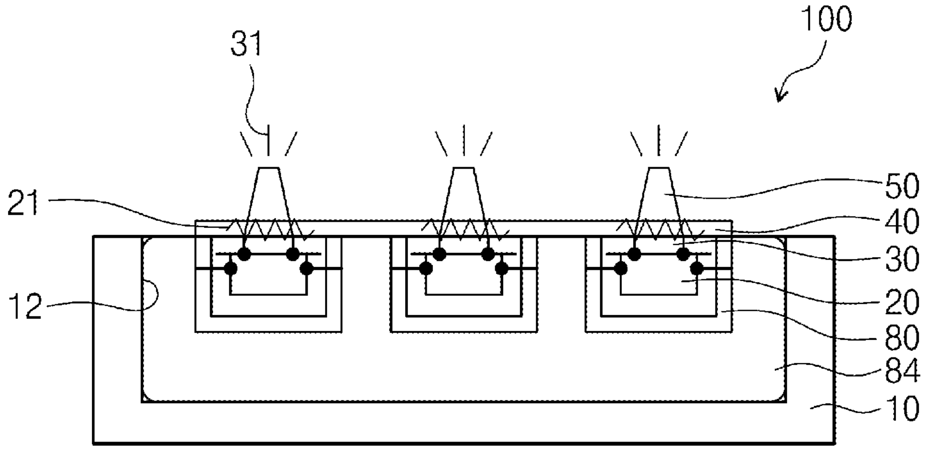
FIG. 19 is a cross-sectional view illustrating an example of the vibration stimulation device according to an embodiment of the inventive concept.

FIG. 19 is a view illustrating an example of the vibration stimulation device 100 according to an embodiment of the inventive concept.

Referring to FIG. 19, the vibrators 20 and the light emitting elements 30 may be disposed in the stands 80, and the stands 80 may be disposed in the elastic body 84. The vibrators 20 may be disposed below the light emitting elements 30. The upper vibration layer 40 may connect the light emitting elements 30 to edges of the stands 80. The bumps 50 may be disposed on the upper vibration layer 40.

The box 10 and the elastic body 84 may be configured as same as those in FIG. 18.

Figure 20:
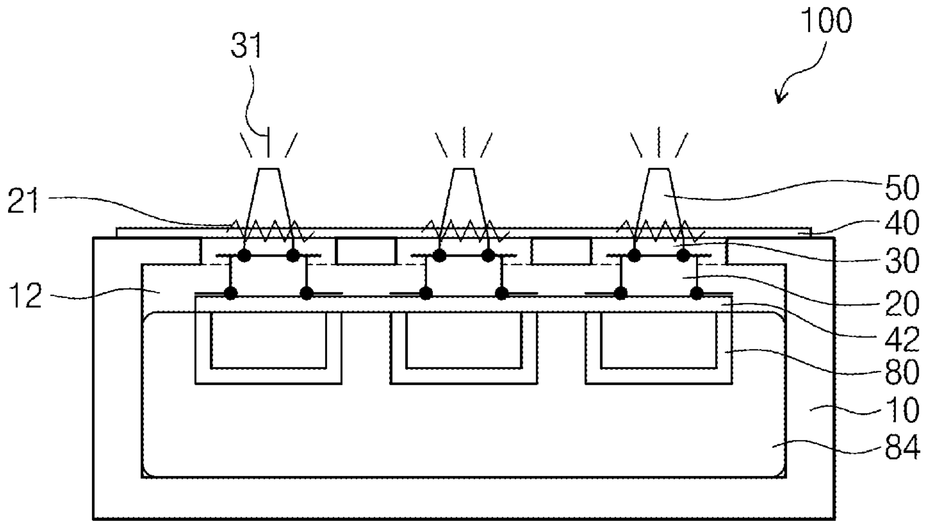
FIG. 20 is a cross-sectional view illustrating an example of the vibration stimulation device according to an embodiment of the inventive concept.

FIG. 20 is a view illustrating an example of the vibration stimulation device 100 according to an embodiment of the inventive concept.

Referring to FIG. 20, the stands 80 may be disposed in the elastic body 84. The lower vibration layer 42, the vibrators 20, the light emitting elements 30, the upper vibration layer 40, and the bumps 50 may be stacked.

The box 10 may be configured as same as that in FIG. 1.

Figure 21:
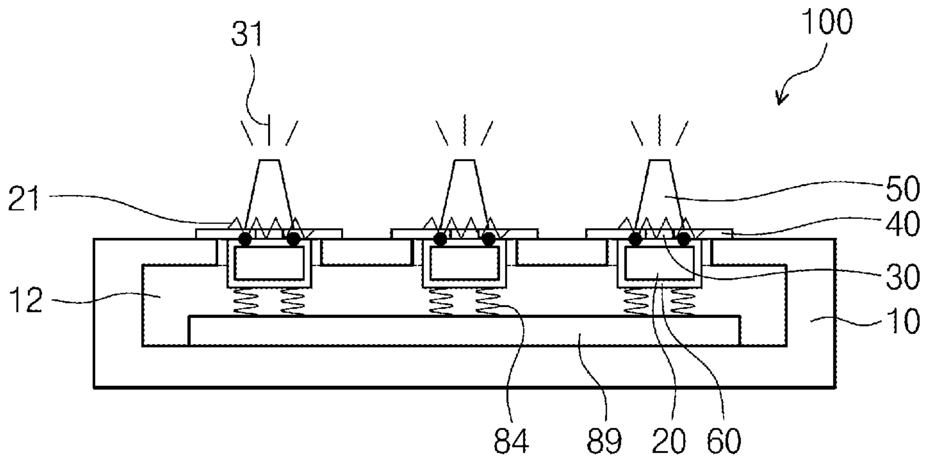
FIG. 21 is a cross-sectional view illustrating an example of the vibration stimulation device according to an embodiment of the inventive concept.

FIG. 21 is a view illustrating an example of the vibration stimulation device 100 according to an embodiment of the inventive concept.

Referring to FIG. 21, the elastic body 84 may include a spring. The spring of the elastic body 84 may be an electric line. The elastic body 84 a serpentine electric line or a loosely connected electric line instead of the spring. A printed circuit board 89 including a printed circuit board or a battery may be disposed in the box 10. The elastic body 84 may be connected to the printed circuit board 89. Although not shown, the elastic body 84 may be connected to the vibrators 20 through the pockets 60.

The pockets 60 may surround the vibrators 20. The light emitting elements 30 may be disposed on the pockets 60 and the vibrators 20. The upper vibration layer 40 may connect the light emitting elements 30, the pockets 60, and the vibrators 20 to a top surface of the box 10. The bumps 50 may be disposed on the light emitting elements 30 and the upper vibration layer 40.

Figure 22:
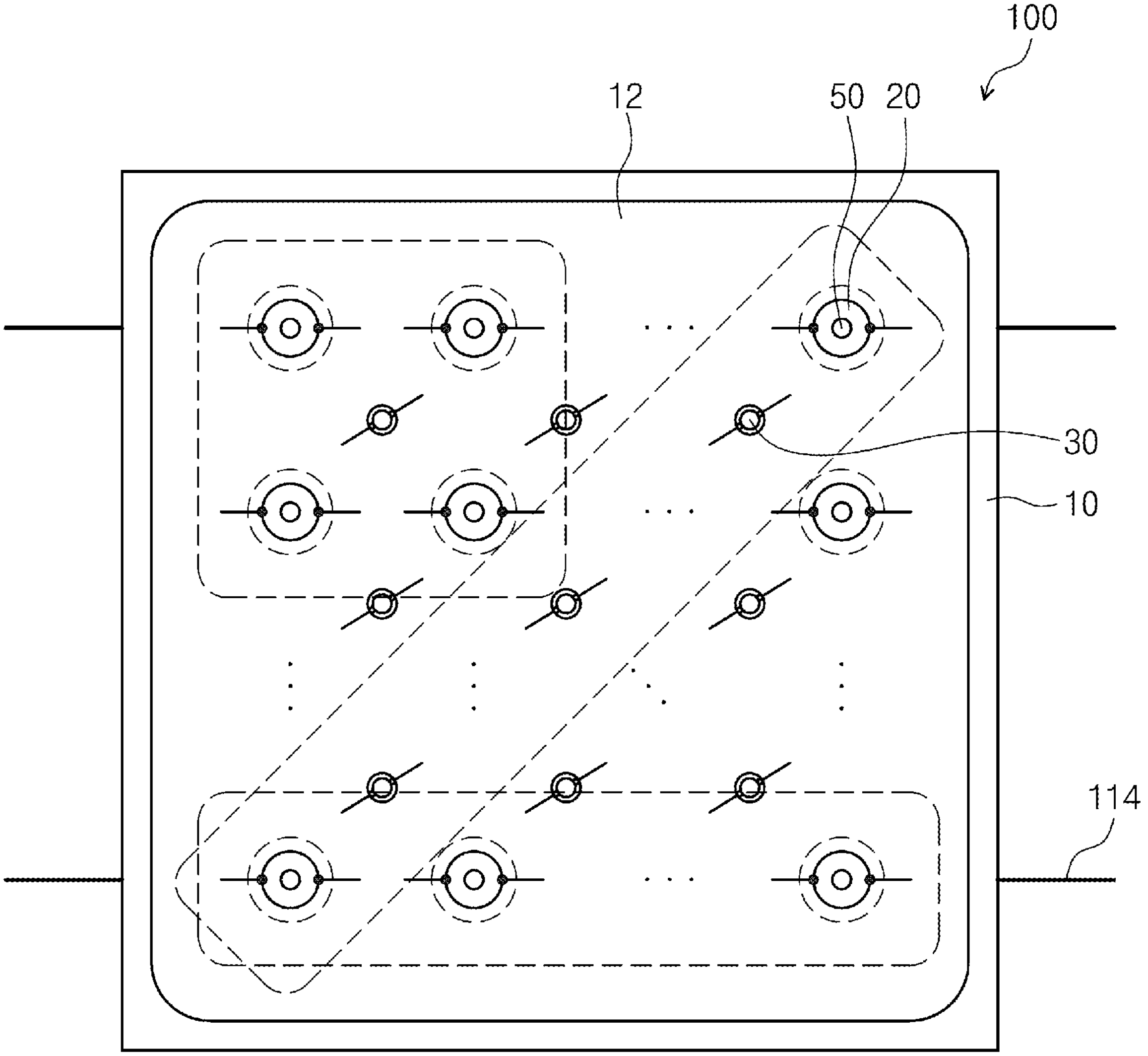
FIG. 22 is a plan view illustrating an example of the vibration stimulation device according to an embodiment of the inventive concept.

FIG. 22 is a view illustrating an example of the vibration stimulation device 100 according to an embodiment of the inventive concept.

Referring to FIG. 22, the box 10 may have a square shape. The vibrators 20 and the light emitting elements 30 may be alternately arranged in a diagonal direction of the square. Bands 114 may be connected to edges of the box 10. The bands 114 may include an electric line. Also, the bands 114 may include fibers or rubber. The bands 114 may include a detachable ring, buckle, Velcro, button, or magnet. However, the embodiment of the inventive concept is not limited thereto.

Figure 23:
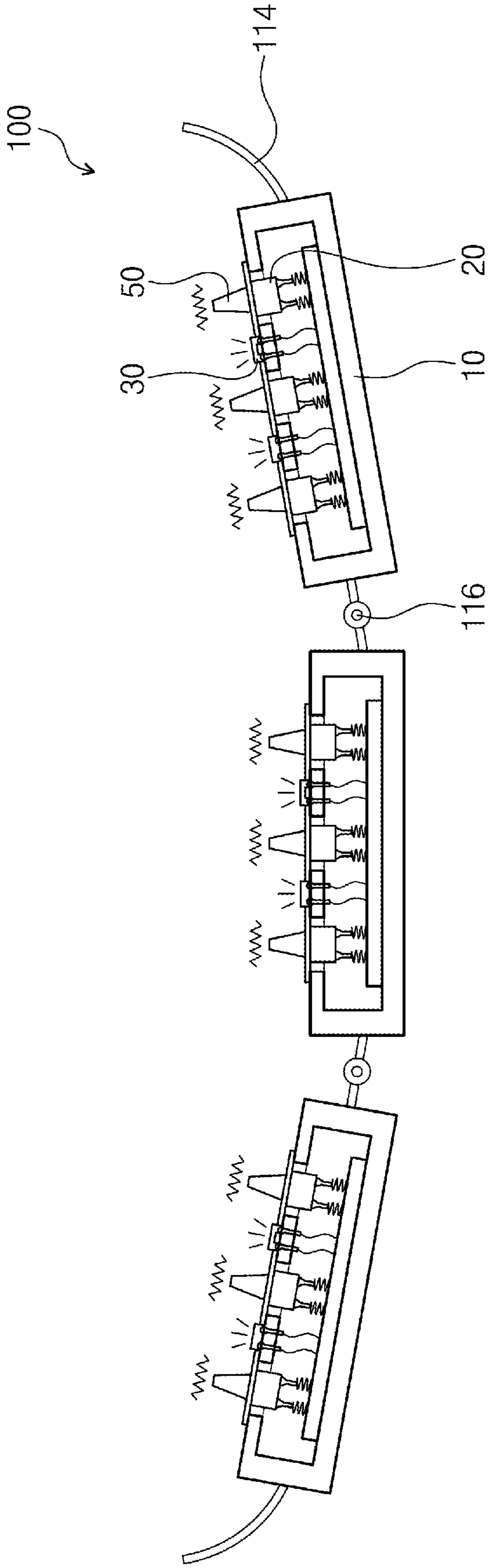
FIG. 23 is a cross-sectional view illustrating an example of the vibration stimulation device according to an embodiment of the inventive concept.

FIG. 23 is a view illustrating an example of the vibration stimulation device 100 according to an embodiment of the inventive concept.

Referring to FIG. 23, the vibration stimulation device 100 according to an embodiment of the inventive concept may further include hinges 116 between the boxes 10. The hinges 116 may assist a rotation movement of the boxes 10 so that the bumps more closely contact a skin. Each of the hinges 116 may include metal or fibers. However, the embodiment of the inventive concept is not limited thereto.

Figure 24:
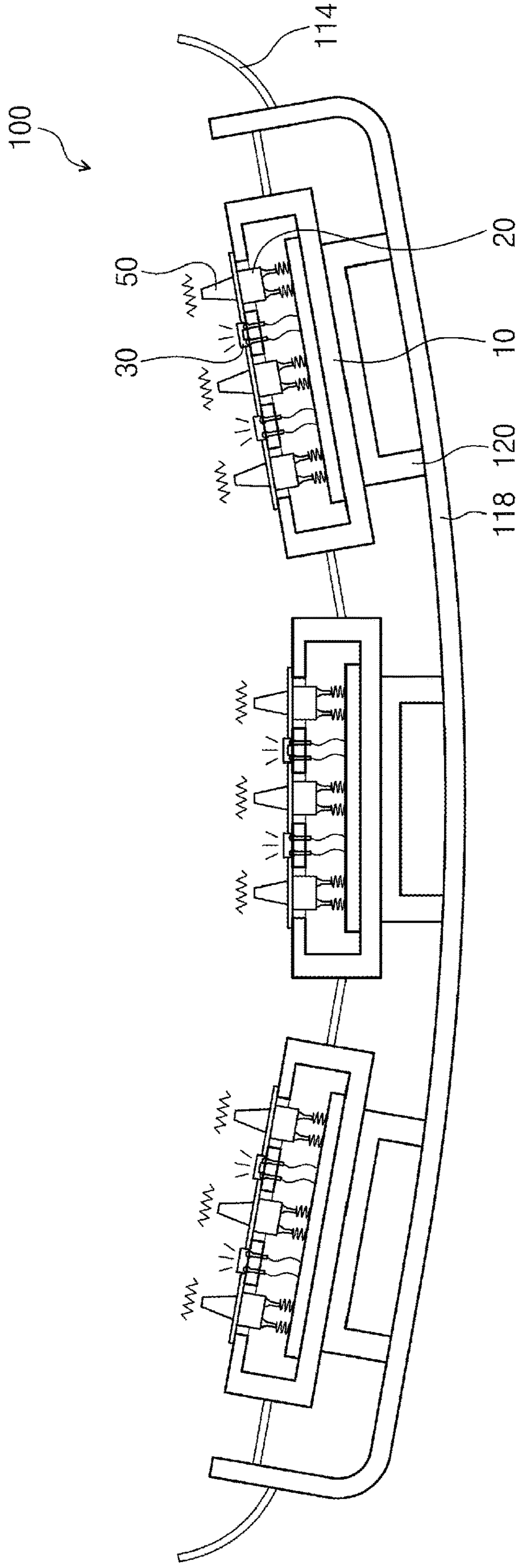
FIG. 24 is a cross-sectional view illustrating an example of the vibration stimulation device according to an embodiment of the inventive concept.

FIG. 24 is a view illustrating an example of the vibration stimulation device 100 according to an embodiment of the inventive concept.

Referring to FIG. 24, the vibration stimulation device 100 according to an embodiment of the inventive concept may further include a case 118 and supports 120. The boxes 10 may be disposed in the case 118. The case 118 may surround the boxes 10 and a lower portion of the bands 114 connected to the boxes 10. The cases 118 may protect and fix the boxes 10.

The supports 120 may be disposed between the boxes 10 and an inner bottom surface of the case 118. The supports 120 may fix the boxes 10 in the case 118. Each of the supports 120 may include a rubber block. However, the embodiment of the inventive concept is not limited thereto.

The vibrators 20, the light emitting elements 30, and the bumps 50 may be configured as same as those in FIG. 1.

Figure 25:
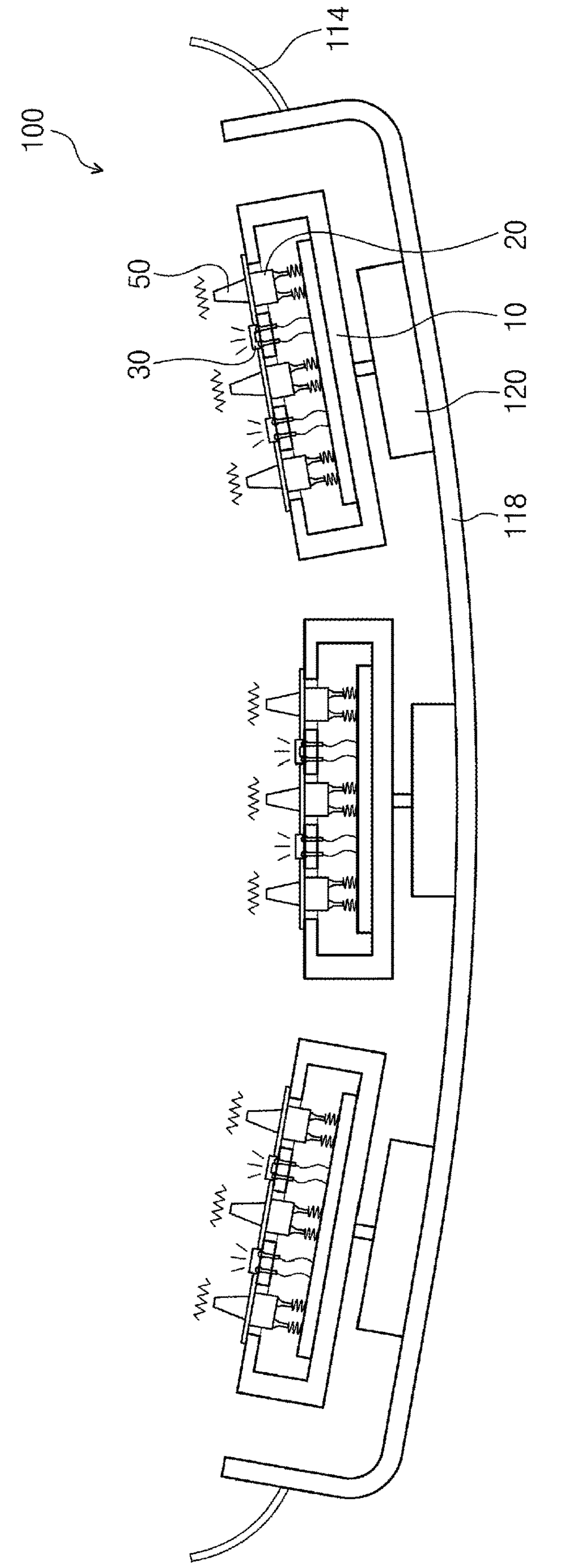
FIG. 25 is a cross-sectional view illustrating an example of the vibration stimulation device according to an embodiment of the inventive concept.

FIG. 25 is a view illustrating an example of the vibration stimulation device 100 according to an embodiment of the inventive concept.

Referring to FIG. 25, rotation shaft supports 120 allowing the boxes 10 to perform a rotation movement may connect a center of each of the boxes 10 to an inner bottom surface of the case 118.

The vibrators 20, the light emitting elements 30, the bumps 50, the bands 114, and the case 118 may be configured as same as those in FIG. 24.

Figure 26:
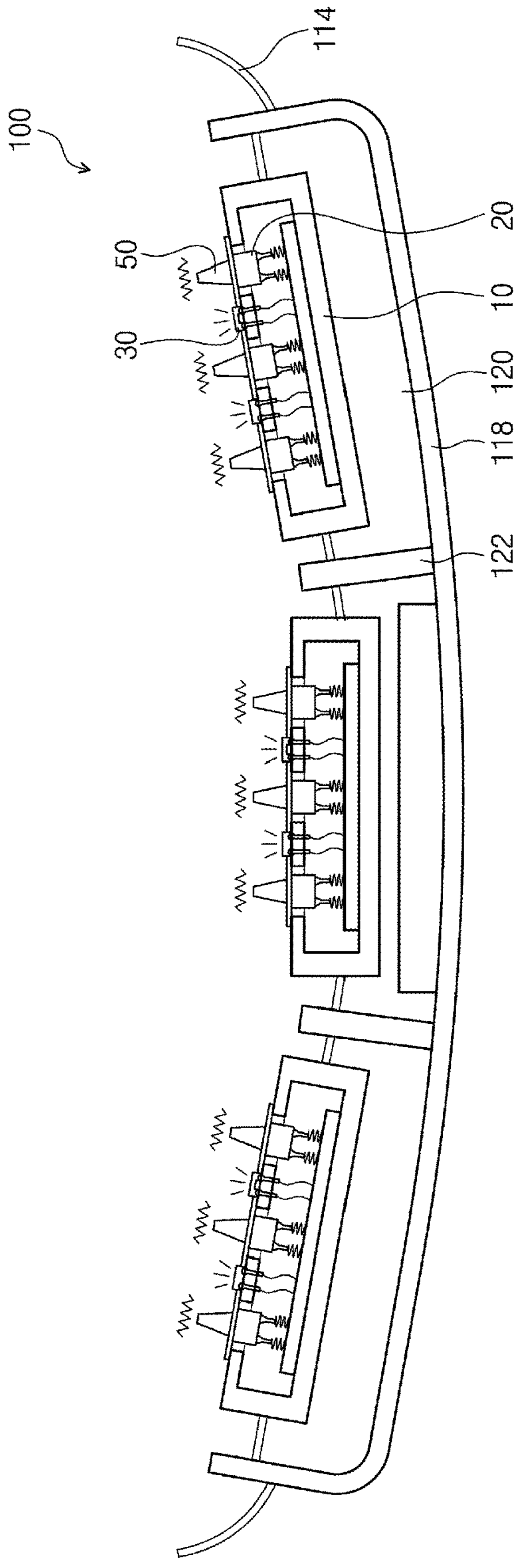
FIG. 26 is a cross-sectional view illustrating an example of the vibration stimulation device according to an embodiment of the inventive concept.

FIG. 26 is a view illustrating an example of the vibration stimulation device 100 according to an embodiment of the inventive concept.

Referring to FIG. 26, partition walls 122 may be disposed between the boxes 10. The partition walls 122 may be connected to the inner bottom surface of the case 118. The partition walls 122 may define a horizontal movement distance of the boxes 10.

The vibrators 20, the light emitting elements 30, the bumps 50, the bands 114, and the case 118 may be configured as same as those in FIG. 24.

Figure 27:
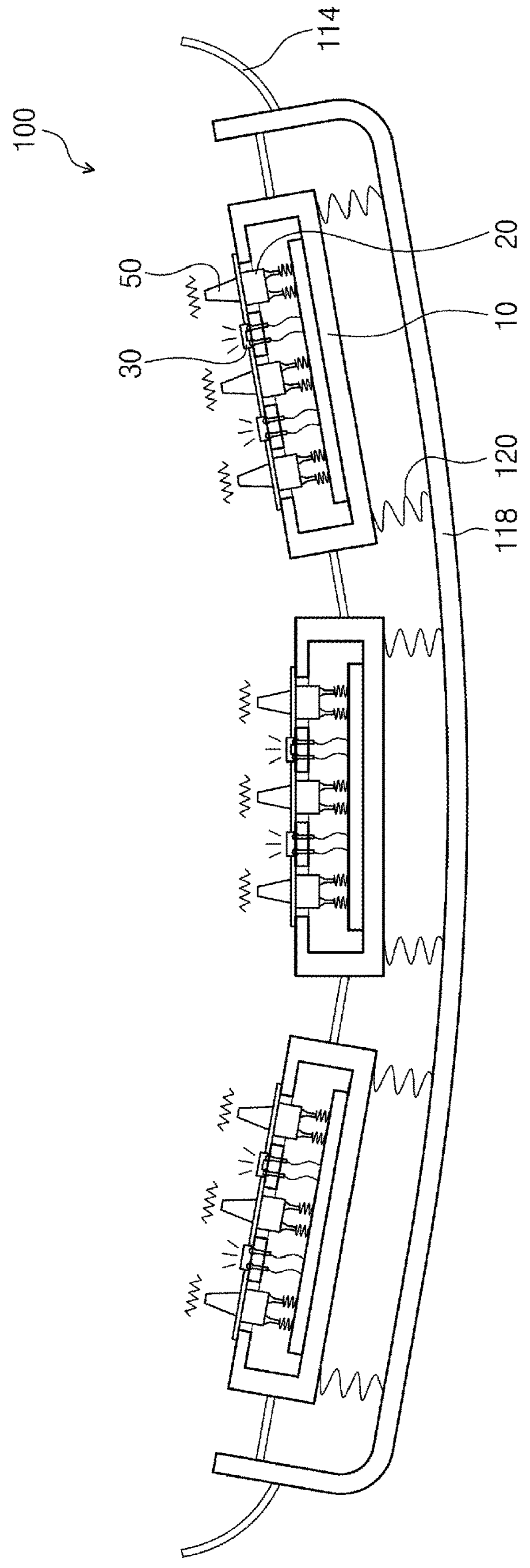
FIG. 27 is a cross-sectional view illustrating an example of the vibration stimulation device according to an embodiment of the inventive concept.

FIG. 27 is a view illustrating an example of the vibration stimulation device 100 according to an embodiment of the inventive concept.

Referring to FIG. 27, the supports 120 may connect edges of the boxes 10 to an inner bottom surface of the case 118. The supports 120 may prevent collision between the boxes 10 and the case 118. Each of the supports 120 may have a spring shape and may be a serpentine electric line.

The vibrators 20, the light emitting elements 30, the bumps 50, the bands 114, and the case 118 may be configured as same as those in FIG. 24.

Figure 28:
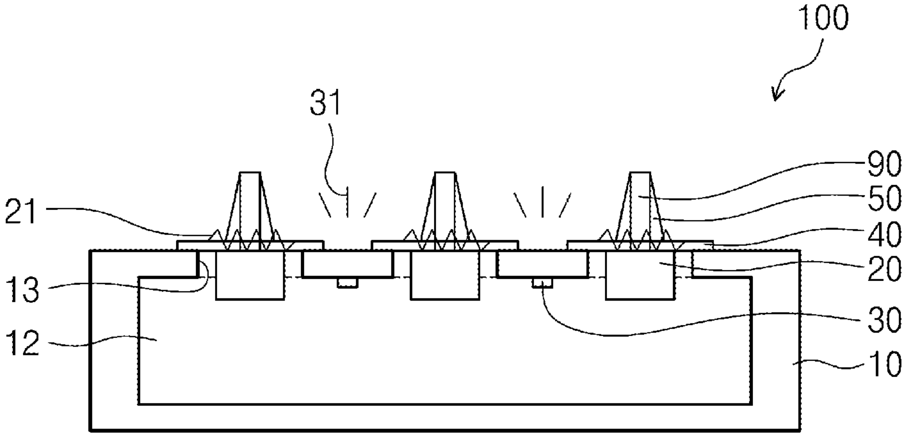
FIG. 28 is a cross-sectional view illustrating an example of the vibration stimulation device according to an embodiment of the inventive concept.

FIG. 28 is a view illustrating an example of the vibration stimulation device 100 according to an embodiment of the inventive concept.

Referring to FIG. 28, the vibration stimulation device 100 may further include thermoelectric elements 90. The thermoelectric elements 90 may be disposed in the bumps 50, respectively. The thermoelectric elements 90 may be disposed between the vibrators 20 and the human body 200. The thermoelectric elements 90 may heat the human body 200 and cool the vibrators 20.

The box 10, the vibrators 20, the light emitting elements 30, and the upper vibration layer 40 may be configured as same as those in FIG. 1.

Figure 29:
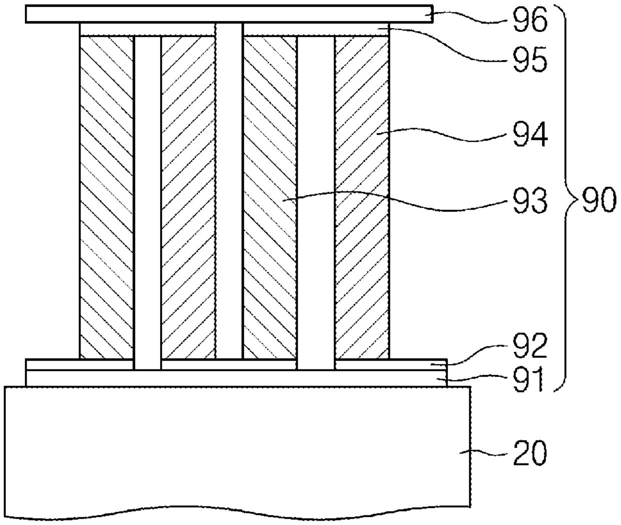
FIG. 29 is a cross-sectional view illustrating an example of a thermoelectric element in FIG. 28.

FIG. 29 shows an example of the thermoelectric element 90 in FIG. 28.

Referring to FIG. 29, the thermoelectric element 90 may include a lower substrate 91, lower electrodes 92, a first-type semiconductor 93, a second-type semiconductor 94, upper electrodes 95, and an upper substrate 96.

The lower substrate 91 may be disposed on the vibrators 20. The lower substrate 91 may include ceramic.

The lower electrodes 92 may be disposed on the lower substrate 91. Each of the lower electrodes 92 may include gold (Au), silver (Ag), copper (Cu), and aluminum (Al).

The first-type semiconductor 93 may be disposed on the lower electrodes 92. The first-type semiconductor 93 may be an n-type semiconductor. The first-type semiconductor 93 may include silicone doped with n-type conductive impurities. Also, the first-type semiconductor 93 may include n-type GaSa or InP. However, the embodiment of the inventive concept is not limited thereto.

The second-type semiconductor 94 may be disposed adjacent to the first-type semiconductor. The second-type semiconductor 94 may be disposed on the lower electrodes 92. The second-type semiconductor 94 may be serially connected to the first-type semiconductor 93 through the lower electrodes 92 and the upper electrodes 95. When the first-type semiconductor 93 is an n-type semiconductor, the second-type semiconductor 94 may be a p-type semiconductor. The second-type semiconductor 94 may include silicone doped with p-type conductive impurities. Also, the second-type semiconductor 94 may include p-type GaSa or InP. However, the embodiment of the inventive concept is not limited thereto.

The upper electrodes 95 may be disposed on the first-type semiconductor 93 and the second-type semiconductor 94. Each of the upper electrodes 95 may include gold (Au), silver (Ag), copper (Cu), and aluminum (Al).

The upper substrate 96 may be disposed on the upper electrodes 95. The upper substrate 96 may include ceramic.

Although not shown, the lower electrodes 92 may be connected to an external power. The power may supply a DC voltage to the thermoelectric element 90 to heat the upper substrate 96 and cool the lower substrate 91. The lower electrodes 92 may be cooled by the Peltier effect, and the upper electrodes 95 may be heated. The human body 200 may be heated and treated. Also, the vibrators 20 may be cooled to prevent deterioration thereof.

As described above, the vibration stimulation device according to the embodiment of the inventive concept may heat and/or treat the human body by using the light emitting elements disposed between the vibrators or the light emitting elements disposed on the vibrators.

Although the embodiments of the present invention have been described, it is understood that the present invention should not be limited to these embodiments but various changes and modifications can be made by one ordinary skilled in the art within the spirit and scope of the present invention as hereinafter claimed. Thus, the above-disclosed embodiments are to be considered illustrative and not restrictive.

What is claimed is:

1. A vibration stimulation device comprising:

a box having a cavity;

vibrators disposed in the cavity;

light emitting elements disposed between the vibrators or disposed on the vibrators;

an upper vibration layer configured to connect the vibrators and the light emitting elements to edges of the box on the cavity;

bumps disposed on the vibrators; and thermoelectric elements disposed on the vibrators and disposed in the bumps, wherein each of the bumps surrounds a side of a corresponding one of the thermoelectric elements, and wherein each of the thermoelectric elements comprises:

a lower substrate disposed on a corresponding one of the vibrators;

lower electrodes disposed on the lower substrate;

first type semiconductors disposed on the lower electrodes;

second type semiconductors disposed on the lower electrodes adjacent to the first type semiconductors, the second type semiconductors connected in series to the first type semiconductors through the lower electrodes;

upper electrodes disposed on the first and second type semiconductors, the upper electrodes connecting the first type semiconductors to the second type semiconductors in series; and an upper substrate disposed on the upper electrodes wherein the upper substrate is exposed at a central portion of each of the bumps.

2. The vibration stimulation device of claim 1, further comprising pockets that respectively surround the vibrators.

3. The vibration stimulation device of claim 2, wherein when the vibrators are disposed on the upper vibration layer, each of the pockets surrounds top and side surfaces of each of the vibrators.

4. The vibration stimulation device of claim 1, further comprising a protection layer disposed on each of the light emitting elements.

5. The vibration stimulation device of claim 1, further comprising a lower vibration layer disposed below the vibrators.

6. The vibration stimulation device of claim 1, wherein each of the bumps has a shape of multiple tips.

7. The vibration stimulation device of claim 1, further comprising weights disposed on or below the vibrators.

8. The vibration stimulation device of claim 7, further comprising weight pockets that respectively surround the weights.

9. The vibration stimulation device of claim 1, further comprising stands disposed between the vibrators and an inner bottom surface of the box.

10. The vibration stimulation device of claim 8, further comprising an elastic body disposed between the stands and an inner bottom surface of the box.

11. The vibration stimulation device of claim 10, wherein the elastic body comprises a rubber block or a spring.

12. The vibration stimulation device of claim 1, wherein the box has trenches disposed below the vibrators.

13. The vibration stimulation device of claim 1, further comprising bands connected to both sides of the box.

14. The vibration stimulation device of claim 1, further comprising:

a case that surrounds a lower portion of the box; and a support disposed between the box and an inner bottom surface of the case.

15. The vibration stimulation device of claim 14, wherein the support comprises a rubber block or a spring.

16. The vibration stimulation device of claim 14, wherein the box is provided in plurality in the case, and the vibration stimulation device further comprises hinges between the plurality of boxes.

17. The vibration stimulation device of claim 1, wherein the box has trenches or recesses which are respectively disposed below the vibrators.

* * * * *